United States Patent [19]

Bascomb et al.

[11] Patent Number: 5,948,612

[45] Date of Patent: Sep. 7, 1999

[54] BIOLOGICAL SCREENS FOR DETECTION OF HERBICIDES

[75] Inventors: Newell F. Bascomb, Lawrenceville, N.J.; Sandra D. Carson, Levittown, Pa.

[73] Assignee: American Cyanamid Company, Parsippany, N.J.

[21] Appl. No.: 08/413,618

[22] Filed: Mar. 30, 1995

Related U.S. Application Data

[63] Continuation of application No. 08/011,000, Jan. 29, 1993, abandoned.

[51] Int. Cl.$^6$ .............................. C12Q 1/68; C12Q 1/02; C12Q 1/18; C12N 9/88
[52] U.S. Cl. .................................. 435/6; 435/29; 435/32; 435/232
[58] Field of Search .................................. 435/6, 15, 29, 435/69.1, 172.3, 193, 252.3, 32, 232; 536/23.2, 23.6

[56] References Cited

U.S. PATENT DOCUMENTS

| | | | |
|---|---|---|---|
| 4,220,466 | 9/1980 | Patel | 504/275 |
| 4,761,373 | 8/1988 | Anderson et al. | 435/172.3 |
| 5,079,143 | 1/1992 | Klein et al. | 435/29 |
| 5,198,599 | 3/1993 | Thill | 800/200 |
| 5,767,366 | 6/1998 | Sathasivan et al. | 800/205 |

FOREIGN PATENT DOCUMENTS

| | | |
|---|---|---|
| 0 478 502 A2 | 9/1991 | European Pat. Off. . |
| 87/05627 | 9/1987 | WIPO . |
| 91/17260 | 11/1991 | WIPO . |

OTHER PUBLICATIONS

Smith et al (1989) Proc. Natl. Acad. Sci USA 86:4179–4183 "Functional expression of plant acetolactate synthase genes in *Escherichia coli*".

Wiersma et al (1990) Mol Gen Genet 224:155–159 "Specific trunctions of an acetolactate synthase gene from *Brassic napus* efficiently complement . . . ".

Babczinski et al (1991) Pestic. Sci 31:305–323 "Mode of action of herbicidal ALS–inhibitors on acetolactate synthase from Green Plant . . . ".

Scannell and Pruess, Naturally Occurring Amino Acid and Oligonucleotide Antimetabolites, Chapter 2, *Chemistry & Biochemistry of Amino Acids*, 3:189–244 (1974).

Tomoda and Ōmura, "New Strategy for Discovery of Enzyme Inhibitors: Screening With Intact Mammalian Cells or Intact Microorganisms Having Special Functions," *The Journal of Antibiotics*, 43(10):1207–1222 (1990).

Garner and Hermann, "Operator Mutations of the *Escherichia coli* aroF Gene," *The Journal of Biological Chemistry*, 260(6):3820–3825 (1986).

Frisch, David A., et al., "Direct Genetic Selection of a Maize cDNA for Dihydrodipicolinate Synthase," *Mol. Gen. Genet.*, 228:287–293 (1991).

Spencer, T.M. et al., "Bialaphos Selection of Stable Transformants From Maize Cell Culture," *Theoretical and Applied Genetics*, 79(5):625–631 (1990).

Last and Fink, "Tryptophan–Requiring Mutants of the Plant *Arabidopsis thaliana*," *Biological Abstracts1* 86(1):4385 (1988).

Maier, Walter. et al., "Effect of Chlorsulfuron, a Potent Inhibitor of Acetohydroxy Acid Synthase on Metabolism of *Claviceps Purpurea*," *Biological Abstracts*, 86(9):AB–1025 (1988).

Muday, G.K. et al., "Regulation of the *Salmonella Typhimurium* aroF Gene in *Escherichia coli*., " *Biological Abstracts*, 90(2):14919 (1990).

Shaner, Dale L. et al., "Potent Inhibitors of Acetohydroxyacid Synthase," *Plant Physiol.*, 76:545–546 (1984).

Kranz and Holm, "Cloning by Function: An Alternative Approach for Identifying Yeast Homologs of Genes from Other Organisms," *Proc. Natl. Acad. Sci. USA*, 87:6629–6633 (1990).

*Primary Examiner*—Robert A. Wax
*Assistant Examiner*—Elizabeth Slobodyansky
*Attorney, Agent, or Firm*—Hamilton. Brook, Smith & Reynolds, P.C.

[57] ABSTRACT

This invention pertains to novel protocols for the screening and rapid identification of compounds that specifically inhibit a predetermined enzyme or metabolic target site or pathway that is specific to plants. Enzymes which are specifically or indirected affected by the novel screens include glutamine synthetase (GS), 3-deoxy-D-arabino-heptulosonate 7-phosphate synthase (DAHP), dihydrodipicolinate synthase (DHPS), acetohydroxyacid synthase (AHAS) and phosphoribosyl anthranilate transferase (PAT). The enzymatic pathways targeted by the novel screening protocols are unique to plants, bacteria and fungi and are present at low levels. Thus, inhibiting these enzymes should present little or no toxicity to humans or animals. The screens provide an efficient and rapid method for assessing the herbicidal potential of test compounds. Lead compounds identified by the novel screening protocols can be used as herbicides to inhibit growth.

5 Claims, No Drawings

BIOLOGICAL SCREENS FOR DETECTION OF HERBICIDES

This application is a continuation of application Ser. No. 08/011,000 filed Jan. 29, 1993, now abandoned.

BACKGROUND OF THE INVENTION

Metabolic pathways for nutritionally essential amino acids have become a prime focus of interest in herbicide discovery during recent years. This interest is due to the discovery of several classes of herbicides that are highly active, have low animal toxicity and were found to inhibit enzymes in these pathways. These herbicides inhibit enzymes in the pathways for branched chain amino acids (inhibited by imidazolinones, sulfonylureas and triazolopyrimidines), aromatic amino acids (inhibited by glyphosate), glutamine (inhibited by bialaphos and phosphinothricin) or histidine (inhibited by amitrole).

In traditional herbicide discovery, a chemical sample is sprayed on a whole plant and the effect of the chemical is scored after a set period of time, typically two to three weeks after application. Compounds that are identified from this approach must then be further characterized as to the spectrum of plants affected, toxicity and site of action. This process requires large amounts of the test compound, is time consuming, expensive and inefficient. Therefore, a rapid, small scale method for screening potential herbicides would be advantageous in herbicide development.

SUMMARY OF THE INVENTION

This invention pertains to novel protocols for the screening and rapid identification of compounds that specifically inhibit a predetermined enzyme or metabolic target site that in most cases is specific to plants. The invention further pertains to microbial strains useful for the screening methods described herein. Enzymes that are specifically or indirectly affected by the novel screens include glutamine synthetase (GS), 3-deoxy-D-arabino-heptulosonate 7-phosphate synthase (DAHP), dihydrodipicolinate synthase (DHPS), acetohydroxyacid synthase (AHAS) and phosphoribosylanthranilate transferase (PAT). Ideally, the enzymatic pathways targeted by the novel screening protocols are unique to plants, bacteria and fungi and are present at low levels. The screens herein described can also target enzymes that are present in animals, for example, glutamine synthatase. Because of significant differences between plants and animals in the forms of these enzymes, or in compound transport, uptake, or degradation, inhibitors of plant enzymes may not necessarily be active against the animal form of the enzyme. Thus, inhibiting these enzymes should present little or no toxicity to humans or animals. The screens provide an efficient and rapid method for assessing the herbicidal potential of test compounds. Lead compounds identified by the novel screening protocols can be used as herbicides to inhibit plant growth.

The methods described herein employ a microbial strain which ideally expresses a bacterial homologue of an essential plant gene product. The microbial strain has a mutation in the gene encoding the bacterial homologue, resulting in its inability to grow without either expressing the plant gene product or the addition of a nutritional supplement. In one embodiment of the present invention, the microbial strain is maintained under two sets of conditions: test conditions which are conditions suitable for growth of the microbial strain expressing the plant gene product, but unsuitable for growth of the microbial strain in the absence of the plant gene product; and reversal conditions which are conditions suitable for growth of the microbial strain in the absence of the essential plant gene product. The microbial cultures grown under these two conditions are then contacted with a compound to be tested for plant growth inhibitory properties. A compound that specifically inhibits the essential plant gene product is identified as a compound which inhibits the growth of the microbial strain under test conditions but does not inhibit growth under reversal conditions.

The methods of the present invention do not require that all the enzymes of the entire essential plant metabolic pathway be expressed within the microbial strain. The methods require the expression of only one enzyme of the targeted plant pathway sufficient to complement the nutritional requirement of the microbial strain.

In addition, the methods of the present invention do not require that the entire essential plant gene product be expressed within the microbial strain. The methods require the expression of only a portion of the plant gene product sufficient to complement the nutritional requirement of the microbial strain. For example, the portion of the plant gene product sufficient to complement the nutritional requirement of the microbial strain can be a fragment of the plant gene product, or a subunit of a holoenzyme.

According to a particular embodiment of the present invention, phosphoribosyl anthranilate transferase is the essential plant gene product targeted in the screen for inhibitory compounds. The microbial strain used in this screen is one which is unable to grow without either tryptophan, or the plant gene product phosphoribosyl anthranilate transferase. According to this embodiment, test conditions are conditions lacking tryptophan and any other compound which allows for growth of a microbial strain defective for phosphoribosyl anthranilate transferase activity. Reversal conditions are conditions which include tryptophan or any other compound which would allow growth of a microbial strain defective for phosphoribosyl anthranilate transferase activity.

In another embodiment of the present invention, acetohydroxyacid synthase is the targeted essential plant gene product, and the microbial strain used is one which is unable to grow without either acetohydroxyacid synthase, or branched chain amino acids which the microbial strain is unable to make in the absence of acetohydroxyacid synthase. Test conditions do not contain the branched chain amino acids required for growth in the absence of acetohydroxyacid synthase, while reversal conditions do contain the required branched chain amino acids.

In a further embodiment of the present invention, 3-deoxy-D-arabino-heptulosonate 7-phosphate synthase is the essential plant gene product targeted in the screen for inhibitory compounds. The microbial strain used in this screen is unable to grow without either 3-deoxy-D-arabino-heptulosonate 7-phosphate synthase, or the amino acids phenylalanine, tryptophan and tyrosine. Test conditions do not contain phenylalanine, tryptophan and tyrosine, while reversal conditions do contain these amino acids.

In yet a further embodiment of the present invention, glutamine synthetase is the targeted essential plant gene product. According to this embodiment, the microbial strain used for the screen is one which is unable to grow without either the expression of glutamine synthetase or the addition of glutamine. Test conditions are absent glutamine, while glutamine is present in the reversal conditions.

According to yet another embodiment of the present invention, the plant essential gene product targeted in a screen for plant-specific inhibitors of plant growth is dihydrodipicolinate synthase. According to this embodiment, the microbial strain used to screen for inhibitors is unable to grow without either the expression of dihydrodipicolinate synthase, or the addition of diaminopimelic acid. Accordingly, test conditions do not contain diaminopimelic acid, while reversal conditions do contain diaminopimelic acid.

Another embodiment of the present invention relates to a method for identifying a mutant essential plant gene product which is resistant to a compound that would inhibit the wild-type counterpart to the mutant gene product. The ability to identify such a mutant gene product, or the microbial strain expressing the mutant gene product, is useful for the production of transformed plants which express the mutant gene encoding the mutant essential gene product. Such plants will be resistant to a compound that would inhibit growth of a similar plant which does not express the mutant gene (i.e., the wild-type plant). According to this embodiment, a microbial strain expressing a mutant gene encoding an essential plant gene product is grown without a nutritional supplement required for growth of the microbial strain in the absence of the wild-type essential plant gene product. Under these conditions, the microbial strain will grow if the mutant essential plant gene product expressed by the microbial strain is capable of complementing the strain's requirement for a nutritional supplement. A microbial strain growing under these conditions is then contacted with a sufficient quantity of a known inhibitor of the wild-type essential plant gene product to cause inhibition of growth of the microbial strain expressing the wild-type gene product. The microbial cells which are able to grow in the presence of the known inhibitor, under these conditions, are cells expressing a mutant essential plant gene product which is resistant to a compound that would inhibit the wild-type essential plant gene product.

Another embodiment of the present invention relates to the use of mutant plant gene products to identify novel inhibitors of plant growth. Mutant plant genes encoding modified forms of an essential plant enzyme resistant to known inhibitors are likely to be resistant to additional members of the same chemical class (determined by the screening methods herein described). However, such mutants would not necessarily be resistant to novel inhibitors, chemically distinct from previously discovered inhibitors. The screens herein described can therefore be used to identify novel inhibitors of mutant, herbicide resistant essential plant gene products.

DETAILED DESCRIPTION OF THE INVENTION

The method herein described allows for the rapid identification of compounds that specifically inhibit a predetermined enzyme or metabolic target site specific to plants, bacteria and fungi. Furthermore, the same biological reagents used in chemical discovery can be used to select for mutants of the target site that would allow for differential crop selectivity based on genetic modification of the crop plant of interest, rather than selectivity based on the fortuitous metabolism of a compound to an inactive metabolite or the exclusion of a compound by a particular crop species.

The method of the present invention relies on the genetic complementation of a microbial defect with a gene of plant origin. According to the methods described herein, a microbial strain is selected or constructed so that it has a genetic defect in an enzyme of interest, resulting in a microorganism that is unable to grow without either nutritional supplementation or genetic modification (e.g., complementation). The genetic defect would be chosen from those which cause auxotrophy in the absence of an exogenously added essential plant product. To restore prototrophy to the microorganism, a plant gene which can complement the defective microbial gene is expressed in the microbe, thereby alleviating the deficiency caused by the genetic defect. The resulting microbe is dependent on either the plant gene, or the plant product of the enzyme encoded by that gene, for growth in minimal media. The microbe can be used to screen for compounds that inhibit the selected plant enzyme. This can be done, for example, by scoring for differential growth on minimal nutrient agar plates that either contain the product of the enzyme of interest, or lack the product. Compounds that inhibit microbial growth in the absence of the product of the enzyme or pathway, but that do not inhibit microbial growth in the presence of the product, can be specifically identified on these plates. The screen can be modified such that an end product of a pathway is used to test for reversal of growth inhibition. The method of this invention can thus be used to identify compounds that inhibit a specific pathway which contains one, or more than one, plant enzyme in the place of a microbial enzyme.

Once an herbicidal compound is identified that inhibits or interferes with proper functioning of the wild-type enzyme, thus preventing the growth of the organism containing the enzyme, resistant mutants can be isolated. For example, a population can be mutagenized in the presence of a concentration of the inhibitor sufficient to inhibit growth of the wild-type organism, and then individuals can be selected from the population that are able to grow, or grow more rapidly than, wild-type organisms.

The screens herein described can be used to identify new inhibitors of plant specific metabolic processes, characterize analogs of plant specific products based on existing chemistry and detect naturally occurring inhibitors of plant specific enzymes. Sources for potential inhibitors can include fermentation broths, partially purified fermentation broths and naturally and synthetically produced compounds.

Potential inhibitors that have been identified as positive in the primary screen, for example organic molecules or fermentation broths, can be evaluated further in a secondary screen by testing the compound against the plant gene-deficient microbial strain that has not been transformed with (i.e., does not express) the plant gene. In that test, true plant product specific inhibitors will not cause growth inhibition. However, inhibitors of microbial homologues of the plant enzymes may still be useful as herbicides.

Lead inhibitors scored as positive in the primary screen and in secondary evaluations can be further tested on plants.

In the examples that follow, five different essential plant gene products are used to develop biological screens for specific inhibitors of target plant enzymes. Each target enzyme represents an essential step in normal plant metabolism, without which a plant cannot grow. In each case the screen employs a microbial strain which cannot grow without either the plant gene product, or nutritional supplementation. The microbial strains used in these assays can be easily constructed using known techniques and without undue experimentation. Examples of some preferred microbial strains include bacterial strains (e.g., *E. coli*, salmonella and cyanobacteria) and yeast.

Also described is an example of a mechanism-based biological screen for inhibitors of mutant, herbicide resistant plant gene products. According to this embodiment, a target enzyme represents an essential step in normal plant metabolism, but the enzyme is a mutant enzyme that is resistant to an inhibitor of the wild-type homologue of the mutant enzyme. Screens according to this method employ microbial strains which cannot grow without either the plant gene product or nutritional supplementation. These microbial stains can, in most instances, be the same as or similar to the strains used to identify inhibitors of the wild-type essential plant gene products, and can be constructed easily according to known techniques and without undue experimentation.

Acetohydroxyacid synthase (AHAS) is the first enzyme specific to the biosynthetic pathway for branched chain amino acid biosynthesis. Acetohydroxyacid synthase catalyzes the condensation of two molecules of pyruvate to form acetolactate, or one molecule of pyruvate and one molecule of α-ketobutyrate to form acetohydroxy-butyrate. In addition to these substrates, AHAS requires thiamine pyrophosphate and flavin adenine nucleotide for enzyme activity and stability. AHAS from plants is feedback inhibited by isoleucine, leucine and valine. The bacterial enzyme homologues (AHAS I and III) are feedback inhibited by valine, whereas the plant homologue (AHAS II) is not.

AHAS is the target site of several known and unrelated classes of herbicides including the imidazolinones, sulfonylureas and the triazolopyrimidines. The imidazolinones and sulfonylureas serve as positive controls for screens of this invention which exploit this enzyme. Because animals do not have the enzymes for the synthesis of branched chain amino acids, and plants require this pathway for growth, these herbicides have low animal toxicity. In addition, the effects of a number of naturally occurring antimetabolites (toxins) have also been reported to be reversed by one or more of the branched chain amino acids as shown in Table I, Scannel, J. P. and Davis L. Preuss (1974). In *Chemistry of Amino Acids, Peptides and Proteins*, Boris Weinstein, ed. Vol 3, pp 189–224.

TABLE I

NATURAL TOXINS REPORTED TO BE REVERSED BY BRANCHED CHAIN AMINO ACIDS

| Toxic Compound | Reversant |
| --- | --- |
| L-2-amino-4,4-dichlorobutanoic acid | Leu |
| L-4-azaleucine | Leu |
| L-2-amino-4-methyl-4-hexanoic acid | Leu, Phe |
| L-2-amino-4-methyl-5-hexanoic acid | Leu > Val, Ile |
| propargylglycine | Met, Leu, Val |
| L-(threo)-3-hydroxyleucine | Leu, Ile, Val and others |
| furanomycin, threomycin | Ile, Val |
| 1-amino-2-nitrocyclopentanecarboxylic acid | Leu |
| 2-(1-cyclohexen-3(R)-yl)-S-glycine | Val, Leu, Ile, Thr and others |
| 1-cyclohexen-3(R)-yl glyoxylic acid | same as above, both TD inhibitors |
| L-2-(2-methylene-1-cyclopropyl)glycine | Leu |

The occurrence of imidazolinone resistant weeds is a concern in the use of the imidazolinone herbicides and other herbicides that inhibit AHAS. By identifying novel compounds that specifically inhibit the resistant form of AHAS it is possible to identify a compound useful for specifically eradicating, for example, imidazolinone resistant weeds. The mechanism-based screen for the identification of AHAS inhibitors is identical to the screen described for identification of inhibitors of wild-type AHAS, except that the genetic defect of the test organism is complemented by the resistant form of AHAS rather than the wild-type form. This screen can, therefore, be used to identify new AHAS inhibitors, characterize analogs based on existing chemistry and detect inhibitors from natural products.

3-Deoxy-D-arabino-heptulosonate 7-phosphate (DAHP) synthase is the first enzyme in the biosynthetic pathway for aromatic amino acid biosynthesis. The mechanism-based screen utilizing this enzyme can identify inhibitors of DAHP synthase from a test sample that may therefore be herbicidal.

The reaction catalyzed by DAHP synthase is the condensation of phosphoenolpyruvate and erythrose-4phosphate to form 3-deoxy-D-arabino-heptulosonate 7-phosphate. The ultimate products from this pathway are the aromatic amino acids phenylalanine, tryptophan and tyrosine. However, in plants this pathway leads to a diverse array of secondary metabolites including lignin, anthocyanic pigments, auxin and antimicrobial phytoalexins (Weiss, U. and J. M. Edwards (1980) *The Biosynthesis of Aromatic Compounds* (Wiley, N.Y.); Hahlbrock, K. and D. Scheel (1989) *Annu. Rev. Plant Physiol Plant Mol. Biol* 40:347–369). The plant DAHP synthase isozymes are not inhibited by aromatic amino acids.

The only natural product currently identified that inhibits DAHP synthase is the phenylalanine analog 2,5-dihydrophenylalanine (Scannel, J. P. and David L. Preuss (1974) *Chemistry and Biochemistry of Amino Acids, Peptides and Proteins*, Boris Weinstein, ed. Vol 3. pp 189–224). However, because this compound might function by feedback inhibition of bacterial enzymes and may not be effective against the plant enzyme, another control may be required in this screen. Other compounds have been identified that can show reversal of growth inhibition by aromatic amino acids, but the site of action is not DAHP synthase.

Glutamine synthetase (GS) is the key enzyme that functions in assimilation and re-assimilation of ammonia in bacterial, fungal and plant cells. This enzyme catalyzes the formation of glutamine from glutamate, ammonia and ATP, and has been found to be the target site of the herbicidal compounds phosphinothricin and bialaphos (a fermentation product). GS is the target site of two commercial herbicides, INCITE® (phosphinothricin) and BASTA®, (bialaphos). Bialaphos was discovered from a natural fermentation broth, as were several other antimetabolites (herbicidal compounds) as detailed in Scannel and Pruess (Scannel, J. P. and David L. Preuss, (1974), In: *Chemistry and Biochemistry of Amino Acids, Peptides and Proteins*, Boris Weinstein, ed. Vol 3, pp.189–244.) (see Table II). Phosphinothricin and bialaphos can serve as positive controls for antagonism of the plant gene product.

TABLE II

KNOWN GS INHIBITORS

Anticapsin
Azaserine
6-diazo-5-oxo-norleucine (DON)
Tabtoxin
Duazomycin B
Bialaphos
Methionine sulfoximine
Phosalacine
Oxetin Dihydrodipicolinate synthase (DHPS) catalyzes the condensation of β-aspartate semialdehyde and pyruvate to form 2,3-dihydrodipicolinate. In this reaction, pyruvate binds to the enzyme first by forming a Schiff base with a lysine residue (Shedlarski, J. G. and C. Gilvarg (1970) *J. Biol Chem.* 245:1362–1373). The enzyme from tobacco, wheat and maize is feedback inhibited by lysine, and to a lesser degree by lysine analogs (Ghislain, M., Frankard, V. and M. Jacobs (1990) *Planta* 180:480–486; Kumpaisal, R., Hashimoto, T. and Y. Yamada (1987), *Plant Physiol.* 85:145-151; Frisch, D. A., Tommey, A. M., Gegenbach, B. G. and D. A. Somers (1991), *Mol. Gen. Genet.* 228:287–293). The enzyme activity is inhibited 90% by 100 mM lysine. The lysine analog S-(2-aminoethyl) L-cysteine was the strongest inhibitor of the tobacco enzyme and showed 50% inhibition at 0.1 mM and 90% inhibition at 0.5 mM (Ghislain, M., Frankard, V. and M. Jacobs (1990) *Planta* 180:480–486).

In fungal, bacterial and plant cells, the enzyme dihydrodipicolinate synthase (DHPS) functions in the synthesis of the nutritionally essential amino acid, lysine. None of the presently available commercial herbicides act by inhibition of DHPS. Because the enzyme is not present in animals, and the fungal pathway for lysine biosynthesis is different from the plant pathway, it is anticipated that inhibitors of DHPS will be non-toxic to animals and specific for plants. The *E. coli* enzyme is only 22% homologous to the plant enzyme at the amino acid level. Most of the compounds referenced by Scannel and Preuss (Scannel, J. P. and David L. Preuss, (1974), In: *Chemistry and Biochemistry of Amino Acids, Peptides and Proteins*, Boris Weinstein, ed. Vol 3, pp.189–244) that are reversed by diaminopimelic acid or lysine have alternative mechanisms of action, or are feedback inhibitors of microbial enzymes. See Table III below.

TABLE III

ANTIMETABOLITES ANTAGONIZED BY DIAMINOPIMELIC ACID OR LYSINE.

L-selenomethionine
L-4-oxalysine
L-2-amino-4-(2-aminoethoxy)-trans-3-butanoic acid
homoarginine
canavanine
azaserine
6-Diazo-5-oxo-L-norleucine The enzyme phosphoribiosyl anthranilate transferase (PAT) catalyzes the reaction after anthranilate synthase in the biosynthetic pathway for tryptophan. Because this enzyme is unique to plant and microbial metabolism, it is anticipated that an inhibitor of PAT will be a potential herbicide with minimal mammalian toxicity. Arabidopsis mutants that lack this enzyme are not able to grow, indicating that this enzyme is likely to be a good herbicide target site.

PAT catalyzes the formation of N-5'-phosphoribosylanthranilate from phosphoribosylpyrophosphate and anthranilate. Plants and microbes that lack this enzyme exhibit blue fluorescence due to the accumulation of anthranilate (o-aminobenzoic acid). During early stages of growth of these mutants on nutrient agar supplemented with tryptophan, the plants grow at a normal rate and look similar to wild-type. However, by 3 to 4 weeks after germination the PAT mutant is dramatically smaller than the wild type and begins to show morphological abnormalities that include crinkled leaves, small petiole, increased business and eventual greatly decreased fertility (Last, R. L. and G. R. Fink (1988) *Science* 240:305–310). Very little information is available on the regulation of this enzyme in planta.

The invention will now be further illustrated by the following non-limiting examples:

EXAMPLES

Example 1

Mechanism-based screen for inhibitors of Glutamine Synthetase (GS)

Materials and Methods

The *E. coli* strain TH16 (Reitzer, L. J. and B. Magasanik, (1986), *Cell* 45:785–792.) lacks GS activity due to a Tn10Kan transposon insertion in the glnA gene. This insertion mutation results in a glutamine requirement for growth, and also results in resistance to kanamycin (conferred by the Tn10Kan transposon).

To reduce exclusion of compounds by the bacterial membrane (i.e., to increase membrane permeability) (Sampson, B. A., Misra, R., and S. A. Benson, (1989), *Genetics* 122:491–501), the GS defect from TH16 was moved into the imp *E. coli* strain (BAS849) by P1 vir-mediated transduction (Miller, J. H., (1972), Experiments in Molecular Genetics, CSH Laboratory, Cold Spring Harbor, N.Y.). The imp mutation confers increased membrane permeability. The resulting strain, designated SC3, shows glutamine auxotrophy and resistance to tetracycline (conferred by the Tn10 transposon).

The GS deficiency of SC3 was complemented by transforming SC3 with the plasmid pGS12. This plasmid is based on the vector pKK233-2 (Pharmacia), which is a low copy number plasmid that has the chimeric bacterial promoter trc for high level expression of genes cloned downstream of the promoter. This plasmid also has the bla gene for resistance to ampicillin. The chloroplastic form of the Pisum sativum GS gene (Tingey, S. V., Tsai, F.-Y., Edwards, J. W., Walker, E. L. and G. M. Coruzzi (1988) *J. Biol Chem.* 263: 9651–9657) was cloned behind the trc promoter with the result that the plant GS protein is produced in *E. coli* harboring this plasmid. The GS deficient *E. coli* strain, complemented with the pea GS gene, has been designated SC3(GS12).

A culture of *E. coli* strain SC3(GS12) is started from a glycerol stock (stored at −80° C.), or from a single colony from a plate, and grown overnight at 30° C. in 50 ml M9ATK liquid media.

Test plates are composed of M9ATK agar and reversal plates are composed of M9ATKG agar, as follows:
Media:
M9ATK Liquid complete:
Bottle 1:
  10 g M9 base powder (GIBCO)
  970 ml distilled water
  Autoclave at 20#, 30 minutes
Add to Bottle 1 before use:
  10 ml 20 % glucose
  10 ml 5% NaCl
  10 ml 0.1M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
  1.0 ml 10 mg/ml kanamycin
M9ATK Agar complete:
Bottle 1:
  10 g M9 base powder (GIBCO)
  470 ml distilled water
  Autoclave in 1 L bottle at 20#, 30 minutes
Bottle 2:
  15 g DIFCO agar
  500 ml distilled water
  Autoclave in 1 L bottle at 20#, 30 minutes Add to Bottle 1 before use:
  10 ml 20 % glucose
  10 ml 5% NaCl
  10 ml 0.01M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
  1.0 ml 10 mg/ml kanamycin
M9ATKG:
  Prepare M9ATK media as described above.
  Add 25 ml of 20 mg/ml glutamine with other additions to Bottle 1.
Test Plates:
1. Combine M9ATK Bottles 1 and 2 (molten) to prepare IL of molten agar media.
2. Cool to 50° C.
3. Add 10 ml of SC3(GS12) overnight culture ($OD_{600}\approx 4$).
4. Pour 150 ml into each 9×9 inch sterile Sumilon biotray (Cat. No. MS12450).
Reversal Plates:
1. Combine M9ATKG Botttles 1 and 2 (molten) to prepare 1 L of molten agar media.
2. Cool to 50° C.
3. Add 10 ml of SC3(GS12) overnight culture ($OD_{600}\approx 4$).
4. Pour 150 ml into each 9×9 inch sterile Sumilon biotray (Cat. No. MS12450).

The medium in the plates is allowed to solidify and dry for 30 minutes. Test samples (25 μl) are applied to both the test plate and reversal plate in sample wells (144, 5 mm diam in 12×12 array). The control herbicide, bialaphos, is applied to each plate using 5 μl of the stock. The plates are incubated overnight at 30° C. and then examined to compare the zones of inhibition on the matched plates. Active compounds show larger zones of inhibition on the test plate than on the reversal plate.

Screen Results

The absorbance ($OD_{600}$) of the overnight culture of SC3(GS12) after a 100-fold dilution is approximately 1.0±0.1. After overnight growth at 30° C. a plate prepared as described above shows complete confluent growth of SC3 (GS12). Bialaphos, the herbicide positive control, shows a zone of inhibition of 8–12 mm.

Twenty-three antimicrobial compounds, obtained from BBL on ¼" paper discs, are used to test SC3(GS12). See Table IV. None of these compounds are antagonized by glutamine.

In addition, a panel of compounds representing diverse, natural product antibiotics is tested against SC3(GS12). See Table V. None of these compounds are antagonized by glutamine.

Also tested is a series of different fermentation media, or broths, that are representative of the media used to culture various organisms. These media are tested for their ability to support growth of non-complemented SC3 in minimal media. The media are tested in microtiter plates.

EXAMPLE 2

Mechanism-based screen for inhibitors of Acetohydroxyacid Synthase (AHAS)
Materials and Methods An *E. coli* strain was constructed that contains deletions for leuB (isopropyl malate dehydrogenase), ilvIH (AHAS III large and small subunits), ilvB (AHAS I large subunit) and also has the imp (increased membrane permeability) mutation. Construction of bacterial strains harboring the imp mutation is described in greater detail in Example 1. The ilvGM locus (AHAS II large and small subunit) is inactive in all K-12 *E. coli* strains. Therefore, this *E. coil* strain, designated SC2, is deficient in AHAS activity and requires the amino acids isoleucine, leucine and valine for growth on minimal medium. These bacterial cells are also resistant to tetracycline and kanamycin, due to the presence of Tn10 and Tn10Kan transposons used to construct the SC2 strains. The Arabidopsis AHAS gene (the isolation and characterization of which are described in *Plant Physiol.* 85:1110–1117 (1987)), was cloned into the bacterial expression plasmid pKK233-2 (Pharmacia). This plasmid is a low copy number plasmid containing the AHAS gene cloned behind the trc chimeric bacterial promoter. The plasmid also has the bla gene for resistance to ampicillin. SC2 cells were transformed with the AHAS expression vector to produce strain SC2/AC201, resulting in complementation of the SC2 AHAS mutations by the Arabidopsis AHAS gene. Complementation allows the cells to grow on minimal media supplemented only with leucine, which is required because of the leuB mutation.

*E. coli* strain SC2/AC201 is started from a glycerol stock (stored at −80° C.) or a single colony from a M9ATKL plate (less than 2 weeks old), and grown overnight at 37° C. in 50 ml M9ATKL liquid medium. Test plates composed of M9ATKL agar and reversal plates composed of M9ATKILV agar are prepared as follows:
Media:
M9ATKL Liquid, complete:
Bottle 1:
  10 g M9 base powder (GIBCO)
  970 ml distilled water
  Autoclave at 20#, 30 minutes
Add to Bottle 1 before use:
  10 ml 20 % glucose
  10 ml 5% NaCl
  10 ml 0.01 M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
  1.0 ml 10 mg/ml kanamycin
  2.0 ml 25 mg/ml L-leucine
M9ATKL Agar, complete:
Bottle 1:
  10 g M9 base powder (GIBCO)
  470 ml distilled water
  Autoclave in 1 L bottle at 20#, 30 minutes
Bottle 2:
  15 g DIFCO agar
  500 ml distilled water
  Autoclave in 1 L bottle at 20#, 30 minutes
Add to Bottle 1 before use:
  10 ml 20 % glucose
  10 ml 5% NaCl
  10 ml 0.1M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
  1.0 ml 10 mg/ml kanamycin
  2 ml 25 mg/ml L-leucine
M9ATKILV agar, complete:
  Prepare M9ATKL media as described above.
  Add 2 ml of 25 mg/ml L-isoleucine and L-valine with other additions to Bottle 1.
Test Plates:
1. Combine M9ATKL Bottles 1 and 2 (molten) to prepare 1 L of molten agar media.

2. Cool to 50° C.
3. Add 10 ml of SC2/AC201 overnight culture (OD$_{600}$≈1).
4. Pour 150 ml into each 9×9 inch sterile Sumilon biotray (Cat. No. MS12450).

Reversal Plates:
1. Combine M9ATKILV Bottles 1 and 2 (molten) to prepare 1 L of molten agar media.
2. Cool to 50° C.
3. Add 10 ml of SC2/AC021 overnight culture (OD$_{600}$≈1).
4. Pour 150 ml into each 9×9 inch sterile Sumilon biotray (Cat. No. MS12450).

Medium in plates is allowed to solidify and dry for approximately 30 minutes. Test samples (25 µl) are applied to both the test plate and reversal plate in sample wells (144, 5 mm diameter in 12×12 array). The control, imazethapyr, is applied to each plate using 5 µl of the stock (10 µM imazethapyr in 50% DMSO/water at 4° C.). The plates are incubated overnight at 37° C. and then examined to compare the zones of inhibition on the matched plates. Active compounds (i.e., compounds which inhibit the activity of AHAS) show larger zones of inhibition on the test plate than on the reversal plate.

Screen Results

The absorbance (OD$_{600}$) of the overnight culture of SC2/AC201 after a 100-fold dilution is approximately 1.0±0.1. After overnight growth at 37° C. a plate prepared as above shows complete confluent growth of SC 2/AC021. Imazethapyr, the positive control, shows a zone of growth inhibition of approximately 10 mm.

As a control, twenty-three antimicrobial compounds listed in Table IV, Example 1, none of which acts by inhibiting AHAS activity, obtained from BBL on ¼" paper discs, are used to test for growth inhibition of SC2/AC201. None of these compounds tested are antagonised by isoleucine and valine. In other words, none of these compounds show a differential effect on growth in the test plate as compared with the reversal plate.

In addition to the antimicrobial compounds listed above, a panel of compounds representing diverse, natural product antibiotics was tested against SC2/AC201. See Table V, Example 1. None of the listed compounds are antagonized by isoleucine and valine

TABLE IV

ANTIMICROBIAL COMPOUNDS TESTED

| Compound | Amt/disc | Compound | Amt/disc |
|---|---|---|---|
| Kanamycin | 30 µg | Lincomycin | 2 µg |
| Nitrofurantoin | 30 µg | Polymixin B | 300 U |
| Nalidixic Acid | 30 µg | Cefamandole | 30 µg |
| Gentamycin | 10 µg | Novobiocin | 30 µg |
| Cefoxitin | 30 µg | Cephaloridine | 30 µg |
| Clindamycin | 2 µg | Colistin | 10 µg |
| Sulfisoxazole | 2 mg | Erythromycin | 15 µg |
| Trimethoprim | 5 µg | Amikacin | 30 µg |
| Chloramphenicol | 30 µg | Tetracycline | 30 µg |
| Triple Sulfa | 1 mg | Penicillin | 10 U |
| Ampicillin | 10 µg | Vancomycin | 30 mg |

TABLE V

NATURAL PRODUCT ANTIBIOTIC COMPOUNDS

| | |
|---|---|
| Phenazine Alpha-COOH | Antibiotic E19085 Alpha |
| Terreic Acid | D42067 Alpha |
| Curvularin | Antibiotic F28249 Alpha |
| Mitomycin A | Antibiotic E19020 Alpha |

TABLE V-continued

NATURAL PRODUCT ANTIBIOTIC COMPOUNDS

| | |
|---|---|
| Caldariomycin | Antibiotic F42248 Alpha |
| 4-dedimethylamino-4-methylamino-anhydrotetracycline | Cycloserine |
| | Isoquinocycline HCl |
| Valinomycin/Miticide | (AA575 Gamma) |
| Blasticidin "S" | Moxidectin |
| Actithiazic Acid/Mycobacidin | Lincomycin HCl |
| Frenolicin (AC860 alpha) | Antibiotic A0341 Beta, |
| Griseofulvin, -5-OH | Hydorchloride |
| Palitantin | Streptogramin/Vertimycin |
| Aspartocin, Na Salt | Monazomycin |
| Antibiotic Z-1220A #3 | Antibiotic AC541, Sulfate |
| Crassin Acetate | Antibiotic A1531 |
| Antibiotic BL580 Alpha | Angustmycin |
| Antibiotic BM782 Alpha-1 | Etamycin, Na Salt |
| Antibiotic C23024 Alpha | Antibiotic BO2964 Complex |
| Antibiotic C08078 Alpha | Mocimycin |
| Avilamycin | Antibiotic A7363 |
| Antibiotic D49194 Alpha | Antibiotic A9537 |
| Antibiotic D49194 Beta-1 | Actinomycin Crude |
| Antibiotic F28249 Omega | Levomycin |
| Aureothin | Antibiotic AM374 #22 |
| Paromomycin, Sulfate | Antiprotozoin/Antiprotozoin |
| Clavacin/Patulin | Fusarinic Acid |
| Copragen I | Antibiotic A4825 |
| Kasugamycin | Antibiotic V241W |
| Chloramphenicol | Antibiotic V214X |
| Bacitracin | Relomycin, LL-AM684 beta |
| Polymyxin-B-SO4 | Amphomysin, Ca |
| Viomycin, Sulfate | Mycorhodin |
| Novobiocin | Antibiotic C19004 Alpha |
| Hygromycin A | Bottromycin |
| Puromycin Aminonucleoside | Antibiotic AF283 Alpha |
| Puromycin HCl | Antibiotic AF283 Beta |
| Nucleocidin | Lemonomycin |
| Antibiotic BP 12 Alpha | Antibiotic B04068 |
| Leucanicidin | Senfolomycin (RA6950 Beta-A) |
| Antibiotic BM123 Alpha, SO4 | Antibiotic RA6950 Beta-B |
| Declomycin HCl | Antibiotic 15E038 Alpha |
| Gibberellic Acid | Nonactin (AE409 Gamma) |
| Alazopeptin | Antibiotic AM31 Beta & Gamma |
| Nystatin | Leucomycin |
| Carbomycin | Usnic Acid |
| Nosiheptide | Neutramcin |
| Netropsin, HCl | Citrinin |
| Avoparcin Sulfate | Geldamycin |
| | Antibiotic BM:123 Gamma, HCl |

Example 3

Mechanism-based screen for inhibitors of imidazolinone resistant forms of acetohydroxyacid synthase (AHAS)

Materials and Methods

The *E. coli* strain SC2, described in Example 2, is an appropriate strain to use in a screen for inhibitors of imidazolinone resistant forms of plant acetohydroxyacid synthase. This strain contains deletions for leuB, ilvIH and ilvB, and an inactive ilvGM locus. In addition, the strain has an increased permeability mutation, imp. See Example 2 for a more detailed description of this strain.

Complementation of the AHAS deficiency of SC2 by an imidazolinone resistant AHAS gene allows the strain to grow on minimal media supplemented with only leucine (required by the leuB mutation). The mutant AHAS gene used to complement the AHAS deficiency in SC2 is cloned or subcloned, for example, in a readily available bacterial expression plasmid.

The media used for test and reversal plates in this screen are the same as those described in Example 2, describing the screen for inhibitors of plant AHAS. The methods are also the same as those described in Example 2, except that the test and reversal plates are inoculated with an overnight culture of a mutant bacterial strain which is deficient for AHAS activity, but which mutation is complemented by an imidazolinone resistant plant AHAS gene (e.g., strain SC2/AC152).

Screen Results

The absorbance ($OD_{600}$) of the overnight culture of SC2/AC152 after a 100-fold dilution is approximately 0.95±0.07. After overnight growth at 37° C., a plate prepared as described in Example 2 and above shows complete confluent growth of SC2/AC152.

Twenty-three antimicrobial compounds obtained from BBL (listed in Table IV, Example 1), none of which acts by inhibiting wild-type plant AHAS activity, are used to test SC2/AC152. None of these compounds are antagonized by isoleucine and valine. In addition to the antimicrobial compounds listed in Table IV, a panel of compounds representing diverse, natural product antibiotics was tested against SC2/AC152. See Table V, Example 1. None of the listed compounds are antagonized by isoleucine and valine.

Example 4

Mechanism-based screen for inhibitors of 3-Deoxy-D-arabino-Heptulosonate 7-phosphate (DAHP) Synthase Materials and Methods The E. coli strain HE628 contains deletions for aroF (tyrosine repressible DAHP synthase), aroG (phenylalanine repressible DAHP synthase) and tyrA (chorismate mutase/prephenate dehydrogenase) (Garner, C. C. and K. M. Herrmann (1985) *J. Biol. Chem.* 260:3820–3825). These cells require tyrosine for growth, but cannot grow on minimal medium supplemented with 40 µg/ml of tyrosine and tryptophan due to feedback inhibition of aroH (tryptophan repressible DAHP synthase) by tryptophan. These cells have been made to have the imp phenotype as described in Example 1. Complementation of HE628 by a plant DAHP synthase, to produce strain HE828/pLW3-210, allows the cells to grow on tryptophan and tyrosine. The *E. coli* strain and potato DAHP synthase, cloned into the bacterial expression plasmid pKK233-2, were supplied by Dr. Klaus Herrmann from Purdue University. The expression plasmid is a low copy number plasmid containing the potato DAHP synthase under the control of the trc chimeric bacterial promoter. The plasmid also has the bla gene for resistance to ampicillin.

An overnight culture of *E. coli* cells (HE628/pLW3-210) is grown at 37° C., with shaking, in 50 ml liquid M9ATT medium starting from a glycerol stock (-80° C) or a single colony from an M9ATT plate. Test plates composed of M9ATT agar and reversal plates composed of M9ATTF agar are prepared as follows:

Media:

M9ATT Liquid, complete:

Bottle 1:
  10 g M9 base powder (GIBCO)
  970 ml distilled water
  Autoclave at 20#, 30 minutes
Add to Bottle 1 before use:
  10 ml 20 % glucose
  10 ml 5% NaCl
  10 ml 0.1M $CaCl_2$
  1 ml 1 M $MgSO_4$
  2.25 ml 50 mg/ml thiamine
  0.75 ml 100 mg/ml ampicillin
  1.6 ml 25 mg/ml L-tryptophan and L-tyrosine M9ATT Agar, complete:

Bottle 1:
  10 g M9 base powder (GIBCO)
  470 ml distilled water
  Autoclave in IL bottle at 20#, 30 minutes
Bottle 2:
  15 g DIFCO agar
  500 ml distilled water
  Autoclave in 1 L bottle at 20#, 30 minutes
Add to Bottle 1 before use:
  10 ml 20 % glucose
  10 ml 5% NaCl
  10 ml 0.01M $CaCl_2$
  1 ml 1 M $MgSO_4$
  2.25 ml 50 mg/ml thiamine
  0.75 ml 100 mg/ml ampicillin
  1.6 ml 25 mg/ml L-Tryptophan and L-tyrosine M9ATTF agar, complete:

Prepare M9ATT media as described above.
Add 1.6 ml of 25 mg/ml L-phenylalanine with other additions to Bottle 1.

Test Plates:
1. Combine M9ATT Bottles 1 and 2 (molten) to prepare 1 L of molten agar media.
2. Cool to 50° C.
3. Add 10 ml of HE628/pLW3-210 overnight culture ($OD_{600}$≈1).
4. Pour 150 ml into each 9×9 inch sterile Sumilon biotray (Cat. No. MS12450).

Reversal Plates:
1. Combine M9ATTF Bottles 1 and 2 (molten) to prepare 1 L of molten agar media.
2. Cool to 50° C.
3. Add 10 ml of HE628/pLW3-210 overnight culture ($OD_{600}$≈1).
4. Pour 150 ml into each 9×9 inch sterile Sumilon biotray (Cat. No. MS12450).

The medium in the plates is allowed to solidify and dry for 30 minutes. Test samples (25 µl) are applied to both the test plate and reversal plate in sample wells (144, 5 mm diameter in 12×12 array). The plates are incubated overnight at 37° C. and then examined to compare the zones of inhibition on the matched test and reversal plates. Active compounds show larger zones of inhibition on the test plate than on the reversal plate.

Screen Results

The absorbance ($OD_{600}$) of the overnight culture of HE628/pLW3-210 after a 100-fold dilution is approximately 1.21±0.04. After overnight growth at 37° C., a plate prepared as described above shows complete confluent growth of HE628/pLW3-210.

As a control, twenty-three antimicrobial compounds with known modes of action that do not include inhibition of DAHP synthase, obtained from BBL on ¼" paper discs, are used to test HE628/pLW3-210. See Table IV, Example 1. None of the compounds tested were antagonized by phenylalanine.

In addition, a panel of compounds representing diverse, natural product antibiotics and a variety of chemical structures was tested against HE628/pLW3-210. See Table V, Example 1. The effects of none of these compounds were antagonized by phenylalanine.

Example 5

Mechanism-based screen for inhibitors of Dihydrodipicolinate Synthase (DHPS)

Materials and Methods

The *E. coli* strain AT997 (Yeh, P., Sicard, A. M. and A. J. Sinskey (1988), *Mol. Gen. Genet.* 212:105–111), lacks DHPS activity due to a mutation in the dapA gene. As a result, this strain requires diaminopimelic acid for growth. The defect is not complemented by lysine because diaminopimelate is also required for cell wall biosynthesis. Therefore, this screen can be run on rich broth rather than minimal media. This strain also harbors the imp mutation, causing increased membrane permeability. Construction of an imp strain is described in Example 1. the genetic defect in the dapA gene in this strain was complemented by transforming the strain with the plasmid pZMDHPS5 (Frisch, D. A., Tommey, A. M., Gegenbach, B. G. and D. A. Somers (1991), Mol. Gen. Genet. 228:287–293), a pUC19 vector containing the maize cDNA for DHPS under the control of the lac promoter. pZMDHPS5 also harbors the bla gene for resistance to ampicillin. The mutant *E. coli* strain harboring the pZMDHPS5 plasmid has been designated DHPS/AT997.

An overnight culture of DHPS/AT997 *E. coli* cells is started from a single colony or from glycerol stock (stored at −80° C.) and grown in 50 ml LBA (Luria Broth Base) with shaking at 37° C.

Test plates of LBA agar and reversal plates of LBADap agar were prepared as follows:

Media:
LBA:
  25 g GIBCO/BRL Luria Broth Base powder
  1 L distilled water
  Autoclave 500 ml in 1 L bottles at 20# for 30 minutes
  When cooled, add 0.5 ml of 100 mg/ml ampicillin stock to each bottle.
LBA Agar:
  25 g GIBCO/BRL Luria Broth Base powder
  15 g Bacto agar
  1 L distilled water
  Autoclave 500 ml in 1 L bottles at 20# for 30 minutes
  Before pouring plates add 0.5 ml of 100 mg/ml ampicillin stock to each bottle.
LBADap Agar:
  25 g GIBCO/BRL Luria Broth Base powder
  15 g Bacto agar
  1 L distilled water
  Autoclave 500 ml in 1 L bottles at 20# for 30 minutes
  Before pouring plates add 0.5 ml of 100 mg/ml ampicillin stock and 25 mg D,L-$\alpha,\epsilon$-diaminopimelic acid (Sigma) to each bottle.

Test Plates:
1. 500 ml LBA agar, molten
2. Cool to 45° C.
3. Add 5 ml of DHPS/AT997 overnight culture ($OD_{600}=1$) to each bottle.
4. Pour 150 ml into each 9×9 inch sterile Sumilon biotray.

Reversal Plates:
1. 500 ml LBADap agar, molten
2. Cool to 45° C.
3. Add 5 ml of DHPS/AT997 overnight culture ($OD_{600}=1$) to each bottle.
4. Pour 150 ml into each 9×9 inch sterile Sumilon biotray.

The medium on the plates is allowed to solidify and dry for 30 minutes. Test samples (25 $\mu$l) are applied to both the test plate and reversal plate in sample wells (144 wells/plate, 5 cm diameter in 12×12 array). The plates are incubated overnight at 37° C. and then examined to compare the zones of inhibition on the matched plates. Active compounds show larger zones of inhibition on the test plate than on the reversal plate.

Screen Results

The absorbance at 600 nm of an overnight culture of DHPS/AT997 in LBA, cultured as described, is approximately 1.0±0.11. Plates prepared as described show confluent growth of DHPS/AT997 after overnight incubation at 37° C.

A series of standard anti-microbial compounds, obtained from BBL on ¼" paper discs, are tested against DHPS/AT997. See Table IV, Example 1. None of these compounds are antagonized by diaminopimelic acid. In addition, a panel of natural product compounds representing diverse antibiotics and chemistry are tested against DHPS/AT997. See Table V, Example 1. None of these compounds are antagonized by diaminopimelic acid.

Example 6

Mechanism-based screen for inhibitors of Phosphoribosyl Anthranilate Transferase (PAT)

Materials and Methods

The *E. coli* strain trpD9923, obtained from *E. coli* Genetics Stock Center, Yale University lacks PAT activity due to a mutation in the trpD gene. This strain requires tryptophan for growth. This genetic defect was complemented by transforming the trpD, *E. coli* strain with the plasmid pACT13, obtained from Dr. Rob Last (Boyce Tompson Institute). pACCT13 is a $\lambda$YES vector containing the Arabidopsis cDNA for PAT under the control of the lac promoter (Rose, A. B., et al., *Plant Physiol.* 100:582–592 (1992)). The mutant *E. coil* strain harboring the PAT gene has also been modified to include the imp mutation for increased membrane permeability (described in more detail in Example 1). pACT13 also contains the bla gene for resistance to ampicillin. The mutant *E. coli* strain with he pACT13 plasmid has been designated PAT/trpD.

An overnight culture of PAT/trpD *E. coli* cells is started from a single colony or from glycerol stock (stored at −80° C.) and grown in 50 ml M9A with shaking at 37° C. Test plates of M9A agar and reversal plates of M9AW agar are prepared as follows:

Media:
M9A Liquid complete:
Bottle 1:
  10 g M9 base powder (GIBCO)
  970 ml distilled water
  Autoclave at 20#, 30 minutes
Add to Bottle 1 before use:
  10 ml 20 % glucose
  10 ml 5% NaCl
  10 ml 0.1M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
M9A Agar complete:
Bottle 1:
  10 g M9 base powder (GIBCO)
  470 ml distilled water
  Autoclave in 1 L bottle at 20#, 30 minutes
Bottle 2:
  15 g DIFCO agar
  500 ml distilled water
  Autoclave in 1 L bottle at 20#, 30 minutes Add to Bottle 1 before use:
  10 ml 20 % glucose
  10 ml 5% NaCl
  10 ml 0.1M $CaCl_2$
  1 ml 1 M $MgSO_4$
  2.25 ml 50 mg/ml thiamine
  0.75 ml 100 mg/ml ampicillin
  2.0 ml 5 mg/ml tetracycline
M9AW agar, complete:
  Prepare M9A media as described above.
  Add 1.6 ml of 25 mg/ml tryptophan with other additions to Bottle 1.
Test Plates:
1. Combine M9A Bottles 1 and 2 (molten) to prepare 1 L of molten agar media.
2. Cool to 50° C.
3. Add 10 ml of PAT/trpD overnight culture ($OD_{600} \approx 1$) to each bottle.
4. Pour 150 ml into each 9×9 inch sterile Sumilon biotray.
Reversal Plates:
1. Combine M9AW Botttles 1 and 2 (molten) to prepare 1 L of molten agar media.
2. Cool to 50° C.
3. Add 10 ml of PAT/trpD overnight culture ($OD_{600} \approx 1$) to each bottle.
4. Pour 150 ml into each 9×9 inch sterile Sumilon biotray.

The medium on the plates is allowed to solidify and dry for 30 minutes. Test samples (25 μl) are applied to both the test plate and reversal plate in sample wells (144 wells/plate, 5 cm diameter in a 12×12 array). The plates are incubated overnight at 37° C. and then examined to compare the zones of inhibition on the matched plates. Active compounds show larger zones of inhibition on the test plate than on the reversal plate.

Screen Results

The absorbance at 600 nm of an overnight culture of PAT/trpD in M9A, cultured as described, is approximately 1.0±0.14. Plates prepared as described show confluent growth of PAT/trpD after overnight incubation at 37° C.

A series of standard antimicrobial compounds, obtained from BBL on ¼" paper discs (see Table IV, Example 1), are tested against PAT/trpD. None of these compounds are antagonized by tryptophan. In addition, a panel of naturally occurring compounds representative of diverse antibiotics and chemistry are tested against PAT/trpD (see Table V, Example 1). None of these compounds are antagonized by tryptophan.

Furthermore, a collection of diverse fermentation media are tested. None of these media support growth of the non-transformed trpD *E. coli* strain nor do they inhibit growth of the trpD or PAT/trpD strains.

Finally, a variety of compounds representing a standard herbicide panel are screened. (see Table VI below). None of the listed compounds are active inhibitors in this screen.

TABLE VI

HERBICIDES

| Compound | Compound |
| --- | --- |
| F3814-525 Perfluidone | Benefin |
| 2-014-1 Oxadiazon | 2,3,5-Trichlorobenzoic acid |
| Simazine (CL15395) | DACTHAL |
| Norea (CL2608) | Desmedipham |
| Monuron | Trifluralin |
| Fenuron | DDT (CL2013) |
| Planavin | Atratone |

TABLE VI-continued

HERBICIDES

| Compound | Compound |
| --- | --- |
| Mefluidide | Concep II |
| CMU (CL14255) | Propazine |
| Paraquat | Trialiate |
| Neburon | Phenmedipham |
| Maleic Hydrazide (CL6374) | Bifenox |
| Silvex Acid (CL35861) | PPG844 |
| Diphenamid (CL87417) | CDEC (Vegedex) |
| Tebuthuiron | Bialaphos |
| Norflurazon | Thiobencarb (Bolero tech) |
| Cypromid | Isopropalin |
| CIPC | Prefar |
| Siduron | Diallate (Avadex tech) |
| Norflurazon | Tillam |
| IPC | CDEA (CL25224) |
| Mefluidide (CL117204), EMBARK | |

Those skilled in the art will recognize, or be able to ascertain using no more than routine experimentation, many equivalents to the specific embodiments described herein. Such equivalents are intended to be encompassed by the following claims.

We claim:

1. A method of screening for a compound or identifying a compound that inhibits an essential plant gene product required for plant growth, said method comprising:
   a) expressing in a microbial strain a plant gene encoding an essential plant product that enables the microbial strain to grow in the absence of a nutritional supplement otherwise required for growth of the microbial strain;
   b) maintaining the microbial strain described in (a) under: (1) test conditions suitable for growth of the microbial strain expressing the essential plant gene product, but unsuitable for growth of the microbial strain in the absence of the essential plant gene product, and (2) reversal conditions suitable for growth of the microbial strain in the absence of the essential plant gene product, thereby producing growing test and reversal cultures of the microbial strain described in (a);
   c) contacting the growing test and reversal cultures produced in (b) with a compound to be tested for plant growth inhibitory properties; and
   d) identifying a compound that inhibits growth of the microbial strain under test conditions but does not inhibit growth of the microbial strain under reversal conditions, said compound being one that inhibits an essential plant gene product required for plant growth.

2. A method according to claim 1, wherein the gene encoding an essential plant product encodes all or a portion of plant acetohydroxyacid synthase.

3. A method of screening for a compound or identifying a compound that inhibits plant acetohydroxyacid synthase, said method comprising:
   a) maintaining a microbial strain expressing a gene encoding plant acetohydroxyacid synthase under:
      (1) test conditions suitable for growth of the microbial strain expressing plant acetohydroxyacid synthase, said test conditions lacking a branched chain amino acid required for growth of the microbial strain in the absence of acetohydroxyacid synthase, and (2) reversal conditions comprising the branched chain amino acid required for growth of the bacterial strain in the absence of acetohydroxyacid synthase, thereby producing test and reversal cultures;

b) contacting the test and reversal cultures produced in (a) with a compound to be tested for plant acetohydroxyacid synthase inhibitory properties; and c) identifying a compound that inhibits growth of the microbial strain under test conditions but does not inhibit growth of the microbial strain under reversal conditions, said compound being one that inhibits plant acetohydroxyacid synthase.

4. A method of screening for a compound or identifying a compound that inhibits an herbicide resistant mutant essential plant gene product required for plant growth, said method comprising:

a) expressing in a microbial strain a mutant plant gene encoding an herbicide resistant essential plant product that enables the microbial strain to grow in the absence of a nutritional supplement otherwise required for growth of the microbial strain;

b) maintaining the microbial strain described in (a) under: (1) test conditions suitable for growth of the microbial strain expressing the herbicide resistant essential plant gene product, but unsuitable for growth of the microbial strain in the absence of the herbicide resistant essential plant gene product, and (2) reversal conditions suitable for growth of the microbial strain in the absence of the herbicide resistant essential plant gene product, thereby producing growing test and reversal cultures of the microbial strain described in (a);

c) contacting the growing test and reversal cultures produced in (b) with a compound to be tested for plant growth inhibitory properties; and d) identifying a compound that inhibits growth of the microbial strain under test conditions but does not inhibit growth of the microbial strain under reversal conditions, said compound being one that inhibits an herbicide resistant essential plant gene product required for plant growth.

5. A method of screening for a compound or identifying a compound that inhibits imidazolinone resistant plant acetohydroxyacid synthase, said method comprising:

a) maintaining a microbial strain expressing a plant gene encoding imidazolinone resistant plant acetohydroxyacid synthase under: (1) test conditions suitable for growth of the microbial strain expressing imidazolinone resistant plant acetohydroxyacid synthase, said test conditions lacking a branched chain amino acid required for growth of the microbial strain in the absence of acetohydroxyacid synthase, and (2) reversal conditions comprising the branched chain amino acid required for growth of the bacterial strain in the absence of acetohydroxyacid synthase, thereby producing test and reversal cultures;

b) contacting the test and reversal cultures produced in (a) with a compound to be tested for imidazolinone resistant plant acetohydroxyacid synthase inhibitory properties; and c) identifying a compound that inhibits growth of the microbial strain under test conditions but does not inhibit growth of the microbial strain under reversal conditions, said compound being one that inhibits imidazolinone resistant plant acetohydroxyacid synthase.

* * * * *